United States Patent [19]

Schneyer et al.

[11] Patent Number: 4,921,808
[45] Date of Patent: May 1, 1990

[54] METHOD FOR DETERMINING FOLLICLE STIMULATING HORMONE

[75] Inventors: Alan L. Schneyer, Delmar; Patrick M. Sluss, East Greenbush; Bosukonda Dattatreyamurty, Albany; Leo E. Reichert, Jr., Loudinville, all of N.Y.

[73] Assignee: The Albany Medical College of Union University, Albany, N.Y.

[21] Appl. No.: 878,159

[22] Filed: Jun. 25, 1986

[51] Int. Cl.$^5$ .......................................... G01N 33/567
[52] U.S. Cl. .................................. 436/503; 436/501; 436/504; 436/543; 436/544; 436/545; 436/804; 436/817; 436/63
[58] Field of Search ............... 436/803, 501, 504, 543, 436/544, 545, 804, 817

[56] References Cited

U.S. PATENT DOCUMENTS

| | | | |
|---|---|---|---|
| 4,016,250 | 4/1977 | Saxena | 514/2 |
| 4,094,963 | 6/1978 | Saxena | 514/2 |
| 4,383,034 | 5/1983 | Sugimoto | 530/399 |

FOREIGN PATENT DOCUMENTS

| | | | |
|---|---|---|---|
| 0108633 | 1/1981 | European Pat. Off. | |
| 8604589 | 8/1986 | PCT Int'l Appl. | 530/399 |
| 2173803 | 10/1986 | United Kingdom | 530/399 |

OTHER PUBLICATIONS

Bhalla et al, TBC, 249, 1984, pp. 43-51.
Stewart et al, J. Endocr., vol. 89, 1981, pp. 213-223.
Reichert & Bhalla, Endocrinol., 94:483-491 (1974).
Reichert et al., J. Clin. Endocrinol, Metab., 41:634-637 (1975).
Reichert & Leidenberger, Ovulation in the Human, Cosignani, P. G., and Mischell, D. R. (eds), pp. 153-166, Academic Press, London (1976).
Minegishi et al., Endocrinol., Japan, 27:717-725 (1980).
Jia et al., J. Clin. Endocronol. Metab., 62:1243-1249 (1986).
Andersen & Reichert, J. Biol. Chem., 257:11551-11557 (1982).
Branca et al., J. Biol. Chem., 260:9988-9993 (1985).
Midgley, J. Clin. Endocrinol. Metab., 27:295-299 (1967).
Schneyer et al., Abstract of Presentation at the 67th Annual Meeting of the Endocrine Society, Jun. 19-21 (1985).
Schneyer et al., Abstract of Presentation at the 18th Annual Meeting of the Society for the Study of Reproduction, Jul. 22-25 (1985).
H. Abou-Issa et al., "Properties of Follitropin-Receptor Interaction", The Journal of Biological Chemistry, 251, 3326-3337 (1976).
Schreyer et al, "Electropharetic Purification of Radiocolinated Fallide-Stimulating Hormone . . . Radioimmunoassay", Endocrinology, vol. 119, 1986, pp. 1446-1453.
Dattatreyamurty et al, "Solubilization of Functional and Stable Fallitropin Receptors . . . Calf Testio", J. Biol. Chem., vol. 261, 1986, pp. 13104-13113.

Primary Examiner—Garrette D. Draper
Attorney, Agent, or Firm—Pennie & Edmonds

[57] ABSTRACT

The present disclosure relates to an improved method based on hormone-receptor binding for the determination of follicle stimulating hormone and to improved reagents useful for the determination of follicle stimulating hormone in a hormone-receptor binding assay.

9 Claims, 5 Drawing Sheets

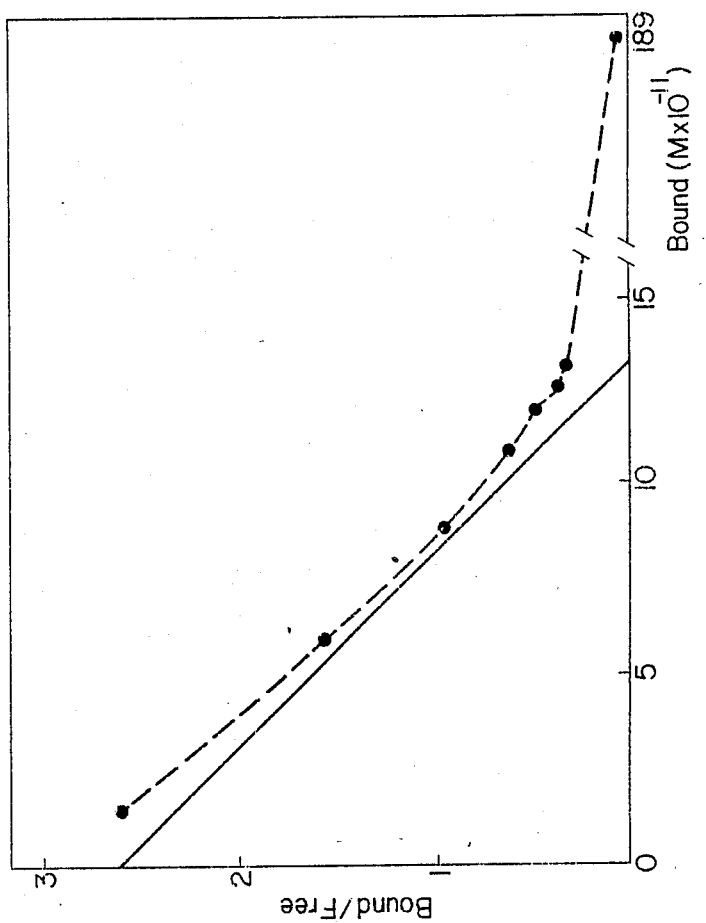
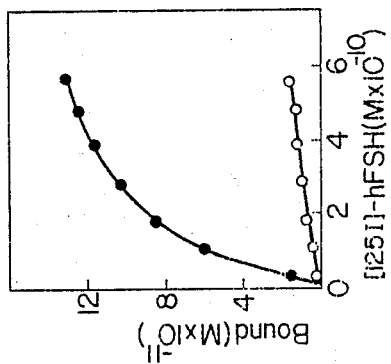
FIG. 1B
FIG. 1A

METHOD FOR DETERMINING FOLLICLE STIMULATING HORMONE

FIELD OF THE INVENTION

The present invention relates to an improved hormone-receptor assay for the determination of follicle stimulating hormone (FSH) and FSH-like material, and to methods for producing substantially pure labeled FSH and the specific fraction of plasma membrane extract containing receptors for FSH in substantially pure form.

BACKGROUND OF THE INVENTION

The present invention relates to a method for the determination of follicle stimulating hormone (FSH) in aqueous solution, particularly body fluids. There are various reasons why it may be desirable to measure quantitatively and qualitatively FSH in a convenient and reliable manner. For example, it may be that the endocrine profile of a patient is needed for assessing the patient's pituitary functions. More commonly, in as much as FSH is necessary for follicle maturation and, therefore, fertility, the determination of a patient's circulating FSH may provide a useful clue to the "female" infertility problem.

The classical test for FSH is the Steelman-Pohley bioassay. It measures, for example, rat ovarian weight gain in response to administration of the hormone. Such bioassays are cumbersome, time consuming and expensive. Moreover, these assays lack precision, and sensitivity: there is a high variability between assays and the lower limit of detectability is in the $\mu g$ range compared to ng levels in, for example, serum. The current assay methods of choice are immunoassays and hormone-receptor binding assays. To perform an immunoassy, FSH must first be injected by suitable techniques into an appropriate test animal to elicit an immunological response and anti-FSH serum must be obtained. There are several common formats in which such an antiserum can be utilized for determining FSH. One commonly used format is competitive inhibition radioimmunoassay. A known amount of radiolabeled FSH, a suitable dilution of the anti-FSH antiserum and varying amounts of a test sample containing FSH are mixed and incubated. Any FSH present in the test sample will compete with the radiolabeled FSH for the available binding sites on the antibodies. If the antibody-antigen complexes are separated from the other portions of the mixture, the radiolabeled FSH recovered from the complexes will be diminished in proportion to the quantity of FSH present in the sample. Alternatively, the radioactivity in the other portions of the mixture will be increased proportionately and can be quantified. This and other formats are based on the specificity of antibody-antigen binding, i.e., on the antibodies' recognition of and affinity for antigenic determinants present in the FSH injected into the test animal. Even severely denatured FSH can be measured with the anti-FSH antiserum because some determinants remain recognizable. Consequently, this method measures both native (biologically active) FSH and denatured or modified (biologically inactive) FSH.

The hormone-receptor binding assay, on the other hand, is based on the specificity of hormone-receptor interaction in the normal physiological context. Thus, a metabolically defective hormone would elicit a positive reaction, i.e., reduce radiolabeled FSH binding, in an immunoassay but not in a receptor binding assay. The converse is true where a factor which inhibits hormone-receptor interaction is to be assayed. Thus, where an inhibiting factor is present, the receptor assay in the standard competitive inhibition format would give a positive reaction because the inhibitory factor, like FSH, will reduce the binding of radiolabeled FSH to the receptors. The inhibitory factor is a "FSH-like material" in this sense. The same inhibitory factor will neither inhibit radiolabeled FSH from binding to anti-FSH antibodies nor compete for the binding sites on those antibodies. Therefore, the inhibitory factor will give a negative reaction in an immunoassay. Generally speaking, the hormone-receptor binding assay is a more specific assay because, in most cases, specific receptor binding at the minimum requires the native conformation of a hormone in its biologically active form.

On a different level, the hormone-receptor binding and the immunoassay share fundamental similarities. Each rests on a ligand-receptor binding mechanism. Therefore, it is possible to utilize all the methodology previously developed for immunoassays within the context of the present invention. In particular, the previously developed signalling mechanisms are applicable. Notable examples are radioligands already referred to, enzyme-linked ligands (preferably linked to an enzyme indirectly through a noncovalent linkage) and ligands linked with a chemical label which may be fluorescent, phosphorescent or otherwise detectable. Accordingly, when the hormone-receptor binding procedure is coupled with a highly sensitive technique, for example, a radioassay, there is obtained a receptor binding radioassay method which possesses the degree of sensitivity of the radioimmunoassay techniques and, at the same time, the selectivity of bioassays. Furthermore, it is clear from the above discussion that a combination of a hormone-receptor binding assay and an immunoassay will provide more complete information than obtainable by each one alone.

Hormone-receptor binding assays have been developed for several hormones. For example, U.S. Pat. Nos. 4,016,250 and 4,094,963 disclose a receptor binding assay method and means for the determination of human chorionic gonadotropin (hCG), leutinizing hormone (hLH) and prolactin (PRL). European Patent Application No. 0108633 discloses improved methods and reagents for the determination of hCG and hLH. A hormone-receptor binding assay exists, albeit in less well developed form, for FSH. For example, Reichert and Bhalla, Endocrinology 94: 483–491 (1974), disclose a hormone-receptor assay for the determination of human FSH in human pituitary gland extracts. Briefly, this FSH assay comprises the steps of (a) contacting a sample suspected of containing FSH or FSH-like material with an agent capable of selectively binding the FSH or FSH-like material, for example, membranes containing FSH-receptors; (b) providing an entity for signalling whether the binding has taken place, for example, radiolabeled FSH; and (c) observing the signalling entity to determine the presence of FSH or FSH-like material in the sample, for example, by detecting the radiation emitted by the radiolabeled FSH which has become bound to the membrane receptors.

The disclosed Reichert and Bhalla method, however, does not work well with serum samples. Serum samples appear to contain small molecular weight interfering materials which interfere in the receptor assay and which can be removed by dialysis. See, e.g., Reichert and Leidenberger, Ovulation in the Human, Crosignani and Mishell (eds.), pp. 153–166, Academic Press, London (1976). Other investigations have found that merthiolate can be used to counter partially the interfering effects observed in receptor assays of serum. Minegishi, Igarashi and Waksbayashi, Endocrinol. Japan, 27(6): 717–725 (1980). The nature of these interfering effects is not clear. Serum may contain a hitherto unrecognized small ligand that binds receptor. It may contain a binding-inhibitory factor or a protease which cleaves off receptors, or some factor which non-specifically blocks the receptors. Notwithstanding all these uncertainties, serum remains the most conveniently obtainable clinical sample. Therefore, it is highly desirable to obtain a simple method and means which can overcome these problems in the determination of FSH, through means which do not require dialysis or other pre-treatment of the serum sample. Dialysis is time consuming, labor intensive and costly. Moreover, dialysis may cause the removal of small molecular weight materials which may be of clinical significance. Example 11 hereinbelow suggests that such materials do exist in serum samples of patients suffering from premature ovarian failure.

Furthermore, normal human serum samples contain about 4 to 25 mIU/ml of FSH. Turner, C. A. and Bagnara, J. T., General Endocrinology, W. B. Saynders & Co., Phila. (1976). Methods in the prior art can detect FSH levels in serum by RIA in excess of 3 mIU/ml but not at all by hormone-receptor binding assay. It is desirable to obtain an improved method and improved reagents for hormone-receptor binding assay that have greater detection sensitivity, and that may be used to assay serum samples.

Recently, Jia et al., J. Clin. Endocrinol. and Metabolism, 62: 1243–1249 (1986), disclosed a method applicable to serum samples. This method, however, has several serious drawbacks. It calls for preparations of explants of granulosa cells from immature rats and an in vitro culture assay that span a period of several days. Moreover, granulosa cells are not permanent cell lines and cannot be maintained indefinitely. Therefore, frequent fresh explants are necessary. Moreover, all serum test samples must be pretreated with polyethylene glycol and clarified by centrifugation to remove "non-specific" interfering materials. All these disadvantages add to the cost and complexity of such a test.

OBJECTS OF THE INVENTION

It is, therefore, an object of the present invention to provide an improved method for the determination of FSH.

Another object of this invention is to provide a method useful for the determination of biologically relevant factors (called "FSH-like material") which inhibit the binding of FSH to its receptor.

Another object of this invention is to provide a sensitive test for determining the presence of biologically active FSH in an aqueous sample, and more particularly, in a very small sample of body fluid, and without prior dialysis or other pre-treatment of such body fluid samples.

Yet another object of this invention is to provide a diagnostic test for differentiation of various infertility problems.

A further object of the present invention is to provide, in substantially pure form, the specific fraction of plasma membrane extract, preferably from calf testes, containing receptors for binding FSH in the test and method referred to above.

It is also an object of this invention to provide a method for producing, in substantially pure form, the specific fraction of plasma membrane extract containing receptors for FSH, particularly from calf testes.

An additional object of the present invention is to provide a substantially pure, labeled FSH useful for signalling the presence of biologically active FSH or FSH-like material, and more particularly, to provide a substantially pure radiolabeled FSH.

Yet another object of this invention is to provide a method for producing the substantially pure radiolabeled FSH or otherwise labeled FSH referred to above.

These objects may be achieved as set forth in greater detail below.

SUMMARY OF THE INVENTION

The invention relates to methods for the determination of follicle stimulating hormone or follicle stimulating hormone-like material in a sample, comprising the steps of:
a. contacting said sample with a binding agent capable of selectively binding said hormone or said hormone-like material;
b. providing a signalling entity for signalling whether said binding has taken place; and
c. observing said signalling entity to determine the presence of said hormone or said hormone-like material in said sample, with the improvement comprising said signalling entity being a substantially pure follicle stimulating hormone labeled with a detectable label, in which labeled hormone the ratio of specific binding to non-specific binding is at least about 5 when measured using a calf testes plasma membrane extract containing from about 5 to about 25 fmol of receptors per milligram of membrane wet weight, and said binding agent having at least about 600 fmol/mg protein of high affinity receptors for follicle stimulating hormone.

Alternately, the signalling entity used in the assay method may be described as follows: a substantially pure follicle stimulating hormone labeled with a detectable label, prepared from an unpurified labeled follicle stimulating hormone in which:
(i) the substantially pure labeled follicle stimulating hormone co-migrates as a single band with unlabeled follicle stimulating hormone when electrophoresed on 7.5% polyacrylamide gel with an acrylamide to BIS ratio of about 19:1 in an electrophoresis buffer containing 9.3 g of Trisma base, 1.2 of ethylenediamine-tetraacetic acid (disodium salt), 0.7 g of boric acid and 5 mg of merthiolate per liter of water at a pH of from 8.9 to 10; and
(ii) when the unpurified, labeled follicle stimulating hormone is chromatographed on a G-25 column and a portion of the labeled follicle stimulating hormone of any fraction from the column having the same amount of detectable label as used in part (i) is electrophoresed as described in part (i), the amount of detectable label found in the single band of part (i) is at least about three times the amount of detectable label in the co-migrating band of material from the fraction of the column.

BRIEF DESCRIPTION OF FIGURES

FIG. 1A shows the binding of [$^{125}$I]-hFSH to calf testes membranes as a function of [$^{125}$I]-hFSH concentration.

FIG. 1B shows a computer Scatchard Plot analysis of the binding data shown in FIG. 1A, to demonstrate the number of receptors present in the membrane preparation.

DETAILED DESCRIPTION OF THE INVENTION

Figure 2B:
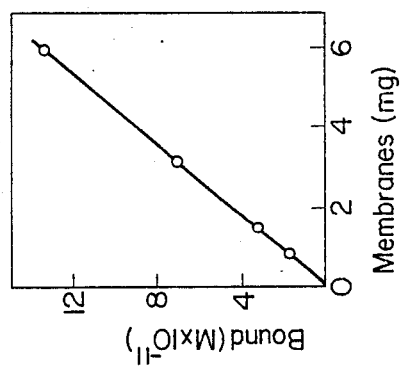
FIG. 2B shows that binding of $^{125}$I]-FSH is proportional to membrane (or receptor) concentration. This figure summarizes the data represented by the isotherms of FIG. 3 illustrates the non-specific interfering effects of "FSH-free" (hypox) serum in the binding of $^{125}$I]-FSH to receptors.

In accordance with the present invention, there is provided an improved method for producing substantially pure FSH labeled with a detectable label. Generally, the method comprises the steps of:

(a) labeling a preparation of follicle stimulating hormone with a detectable label;

(b) electrophoresing the labeled follicle stimulating hormone in a polyacrylamide gel;

(c) locating and excising, after electrophoresis, that part of said polyacrylamide gel which contains labeled follicle stimulating hormone having substantially the same electrophoretic mobility as the native follicle stimulating hormone; and (d) eluting the labeled follicle stimulating hormone.

The starting material is a preparation of FSH. It is not critical that this initial preparation be highly purified. For example, the electrophoretic procedure described below will remove most contaminants that will adversely affect the FSH determination procedure. The electrophoretic procedure is superior to the procedures practiced in the prior art, for example, G-25 gel filtration, in resolving power. It is, however, preferred that the starting material used in the electrophoresis has been purified to some degree. The method by which the starting material is purified is also not critical. There are several conventional procedures for partial purification of FSH. See, for example, L. E. Reichert and A. K. Parlow, Endocrinol. 74: 236 (1964). The source of FSH is not critical. The present invention has been used to produce substantially pure, labeled FSH from human, cow, rat, sheep, pig, dolphin and porpoise. In a preferred embodiment the starting material has a specific activity of about 4000 IU/mg as determined by the Steelman-Pohley assay.

The starting material can be labeled with a detectable label using a variety of techniques well known in the art. The labeling technique can be a chemical labeling or an enzymatic labeling technique. Examples of the former are the Chloramine-T method and the derivatization method using a N-hydroxysuccinyl ester linkage. An example of the latter is the modification of a polypeptide at a tyrosine residue using lactoperoxidase. Still other techniques can be devised. A preferred labeling technique for FSH is $^{125}$I or $^{131}$I radiolabeling by lactoperoxidase. This method is gentler than, for example, the Chloramine-T technique. Reichert and Bhalla, Endocrin. 94: 483–491 (1974). In general, the gentler the technique, the greater the recovery of biologically active, labeled FSH. Also, radiolabeling is a preferred labeling method because radiation detection is very sensitive and ordinarily does not require further reactions such as enzymatic amplification for measurement. Of course, this is true only if a minimum specific activity is achieved.

After the labeling reaction, the reaction products contain many undesirable materials. These undesirable materials include free label, the labeling reagent, labeled and unlabeled impurities endogenous to starting material and labeled and unlabeled products generated in the reaction which are not biologically active FSH. Many of these undesirable products probably interact with serum, thereby causing interfering effects observed in the prior art. In the present invention, significant improvements in the selective removal of undesirable materials are achieved, as indicated by substantial reduction "non-specific" binding to receptors.

In a preferred embodiment, the reaction product is subjected to polyacrylamide gel electrophoresis (PAGE). PAGE separates a mixture of molecular species largely by size and charge. It is commonly known in the art that the concentration of acrylamide and the degree of cross-linking of the gel determine the range of molecular sizes within which spatial resolution is optimal. Conversely, the desired range of molecular sizes to be resolved determines the gel composition of choice.

Since biologically active FSH must assume a conformation which highly resembles that of native FSH, many biologically active species of labeled FSH are expected to have only a small number of labels on the molecule. Where the molecular weight of the label is small, many biologically active species of labeled FSH will have an apparent molecular weight substantially the same as that of native FSH, namely, about 38,000 daltons by electrophoresis. (Molecular weight of FSH as determined by gel filtration and analytical centrifugation is 33,000 daltons.) Where the molecular weight of the label is not small enough to be insignificant, adjustments must be made to estimate the apparent molecular weights of biologically active species of labeled FSH. Labels of small molecular weight and size are preferred over labels of large molecular weight because the latter tend to affect molecular conformations more. In a preferred embodiment, biologically active species of labeled FSH have apparent molecular weights of approximately 38,000 daltons. Under these conditions, the useful range of acrylamide concentration is then 5–12.5%.

A preferred gel composition is 7.5% acrylamide and a acrylamide to BIS ratio of 19:1.

The composition of the electrophoresis buffer must be such that the buffer will not destroy or otherwise affect the biological activity of FSH. A preferred electrophoresis buffer is given by the chemical formulation: about 9.3 g of Trizma base [tris(hydroxymethyl)aminomethane, Sigma Chemical Co., St. Louis, MO], about 1.2 g of EDTA, about 0.7 g of boric acid and about 5mg of merthiolate in 1 liter of water. The electrophoretic parameters are not critical to the present invention and can readily be adjusted to suit the convenience of the preparer. A preferred set of parameters is: gel length, 125 mm;, 20 milliamp and 50–60 µg of reaction product per sq. cm. of cross-sectional gel area; time of electrophoresis, 1.5 hrs.

After electrophoresis, the gel is cut into slices and the labeled FSH is eluted from each slice. Any standard gel elution method can be used. The appropriate eluted fractions are pooled. In one embodiment, a sample of native FSH may be run alongside the labeled FSH. The native FSH is located and the corresponding area containing labeled FSH can be excised and the labeled FSH eluted. The more limited the selected area, i.e., the smaller the slice, the more homogeneous the eluted labeled FSH will be. On the other hand, the volume of labeled FSH recovered is correspondingly smaller. In a preferred embodiment several slices are made and the eluted fraction from each slice is tested. Suitable fractions are pooled.

Generally, a method for preparing substantially pure, labeled follicle stimulating hormone, comprises the steps (a) labeling a preparation of follicle stimulating hormone with a detectable label;

(b) electrophoresing the labeled follicle stimulating hormone in a polyacrylamide gel;

(c) cutting said polyacrylamide gel after electrophoresis into slices of less than 10%, or preferably less than 3%, of the length of said polyacrylamide gel in a direction perpendicular to the direction of electrophoresis;

(d) eluting separately the labeled follicle stimulating hormone contained in each gel slice of step (c);

(e) measuring the specific binding and the nonspecific binding of each eluant of step (d) containing labeled follicle stimulating hormone to a calf testes plasma membrane extract containing approximately 5 to 25 fmol of receptors per mg of membrane wet weight; and (d) pooling those eluants which have a specific binding to nonspecific binding ratio of at least about 5.

For testing the eluted fractions, "crude" calf testes membranes containing FSH-receptors are prepared. A method known in the prior art is provided in Branca et al., J. Biol. Chem. 260:9988–9993 (1985). Uniform preparation of membranes containing $11.1 \pm 1.2$ fmols of receptors/mg (wet weight) or about 100 fmol of receptors/mg of protein can be routinely obtained. The conditions for the binding reaction are described in Example 8 below. Radiolabeled FSH that gives a specific binding of 25% or greater to such "crude membranes" and a non-specific binding of 5% or less are suitable for the purpose of performing serum assays. The basis for this selection lies in the fact that (1) nonspecific binding increases rapidly for radiolabeled FSH obtained from fractions that fall outside this range (FIG. 5C), and (2) G-25 chromatographed, radiolabeled FSH which is unacceptable for assay of serum samples has a mean specific binding and mean non-specific binding of $18.9 \pm 4.5\%$, and $7.9 \pm 2.9$ respectively.

The significant difference between electrophoretically purified, radiolabeled FSH and G-25 chromatographed, radiolabeled FSH is not the merely arithmetical difference in the specific binding and non-specific binding but the selective removal of certain materials in the radiolabeling reaction product, which materials preferentially interfere with FSH-receptor binding assays when serum samples are used. The preferential removal of interfering materials is reflected in the increase of the specific binding to nonspecific binding ratio. When measured using a calf testes plasma membrane extract containing from about 5 to about 25 fmol of receptors per milligram of membrane wet weight under standard conditions described in Example 8, the ratio for electrophoretically purified, radiolabeled FSH is at least about 5. The ratio for G-25 gel chromatographed, radiolabeled FSH is about 2.2 to 2.9.

Another measure of the selective removal of interfering materials from electrophoretically purified, radiolabeled FSH is shown by displaying the spectra of molecular species of electrophoretically purified, radiolabeled FSH and of G-25 gel chromatographed radiolabeled FSH, respectively, on a gel by electrophoresis. Under the same conditions of electrophoresis as those where the electrophoretically purified, radiolabeled FSH was initially prepared, the electrophoretically purified, radiolabeled FSH is, as expected, substantially homogeneous. The G-25 gel chromatographed radiolabeled FSH, on the other hand, is highly heterogeneous. In particular, a substantial fraction of the radioactive preparation is in the region where the subunits of FSH migrate. If a preparation of electrophoretically purified, radiolabeled FSH is compared to a preparation of G-25 gel chromatographed, radiolabeled FSH containing same total radioactivity, the substantially homogeneous, electrophoretically purified, radiolabeled FSH has at least about three times the radioactivity in the comigrating band from the G-25 chromatographed preparation.

Figure 5A:
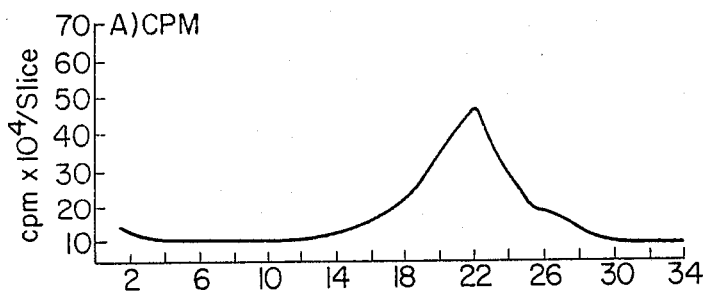
FIG. 5 illustrates the binding profiles of [$^{125}$I]-hFSH eluted from 3 mm gel slices following polyacrylamide gel electrophoresis (PAGE). A) Typical radioactivity profile of gel slices showing peak at fraction 22; B) Specific and non-specific antibody binding profiles for fractions within the iodination peak. Specific antibody binding peaks at fraction 21, subsiding rapidly after fraction 23; C) Specific and non-specific receptor binding profiles for same Specific binding is maximal at fraction fractions as in B. 22, decreasing substantially after fraction 23. Non-specific binding increases rapidly after fraction 23 from a minimum at fraction 21-22. Based on binding data, suitable in RRA of FSH. fractions are pooled for use
Figure 5B:
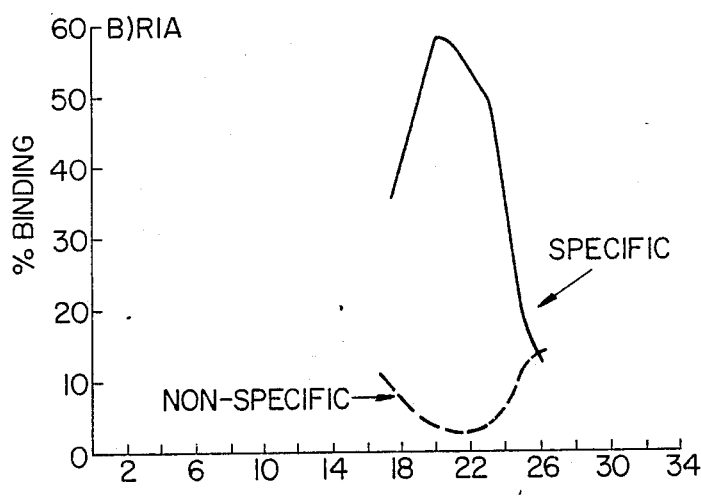
Figure 5C:
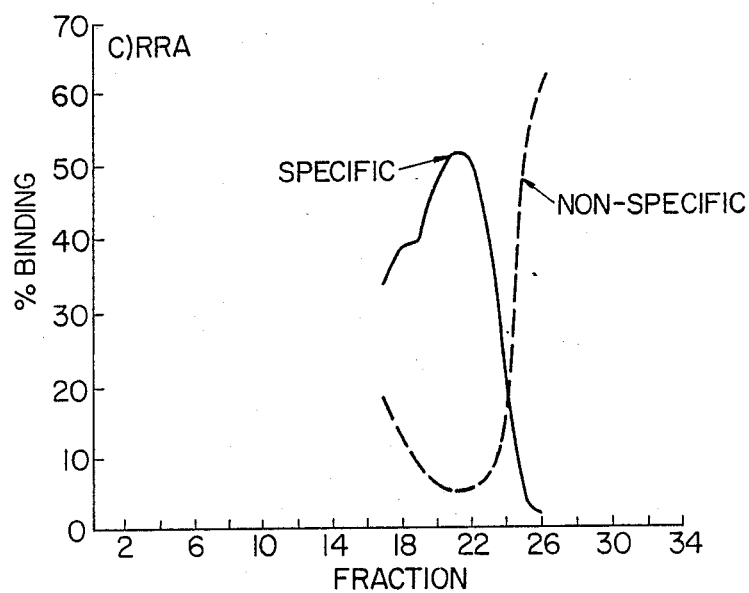

Generally, the G-25 chromatography is as described in Branka et al., J. Biol. Chem. 260: 9988–9993 (1985), in which the fraction volume is about 1 milliliter. The electrophoresis conditions for the substantially pure labeled FSH and the G-25 chromatographed, labeled FSH are as follows: 7.5% polyacrylamide gel with an acrylamide to BIS ratio of about 19:1 in an electrophoresis buffer containing 9.3 g of Trizma base, 1.2 g of ethylenediamine-tetraacetic acid (disodium salt), 0.7 g of boric acid and 5 mg of merthiolate per liter of water at a pH of from 8.9 to 10. Of significance is the fact that this rapid increase of non-specific binding is not observed in radioimmunoassays (FIG. 5B).

For the purpose of testing the eluted fractions, it has been found that membranes containing 5 to 25 fmol of receptors/mg wet weight are substantially the same as those containing $11.1 \pm 1.2$ fmols of receptors/mg wet weight.

For the purpose of performing the serum assays of this invention, "purified" membranes are obtained from "crude" membranes in substantially pure form. The strategy for purification is generally applicable to "crude" membranes from various sources including rat testes, calf testes, granulosa cells from ovaries of various species and several cultured gonadal cell lines. However, calf testes are highly preferred sources because they have a higher concentration of receptors than obtainable from other sources and they are readily commercially available. The "crude" membranes are subjected to a purification procedure which is a combination of sucrose gradient centrifugation and dialfiltration. Although both sucrose gradient centrifugation and dialfiltration are conventional techniques, extensive experimentation has been done in the present invention to determine the optimal conditions for obtaining the membranes which are in substantially pure form, and which can be used for assaying serum samples. The purification procedure, given in Example 7, purifies "crude" membranes ten-fold, and represents the best mode of practice The purified membranes contain about 773±121 fmols/mg protein or at least about 600 fmol/mg protein of high affinity receptors for FSH. (The denominator of the units for concentration of receptor, i.e., mg protein, refers to the weight of membrane associated proteins.) It is expected that membranes of whatever origin, e.g., testes or granulosa cells of various mammalian species, of similar purity can be used for serum assays.

The PAGE purified radiolabeled or otherwise labeled FSH and the purified membranes referred to above can be used in methods which are known in the prior art for the determination of FSH. A common method, based on competitive inhibit ion, is illustrated in Example 9. More importantly, where serum samples are to be tested, the combination of PAGE purified radiolabeled or otherwise labeled FSH and the "purified" membranes must be used. Substitution of either improved reagent by a corresponding agent in the prior art will lead to substantially inferior results. In addition, while hormone-receptor binding assay conditions known in the prior art are adequate, it is highly recommended that HEPES be preferred over Tris-HCl or sodium phosphate as a buffer to improve maximal FSH-receptor binding and to minimize "non-specific" binding, that EDTA be included in the buffer to inhibit proteases in the serum and that ovalbumium or other proteins be included in the buffer to reduce binding of reagents to assay tubes or pipettes. It is also preferred to increase the time period for incubation because serum samples have higher viscosity and delay substantially the time when equilibrium or when "steady state" is reached. ("Steady State" is reached when there is no increase of hormone binding with time.) This improved method provides reliable results with serum test samples, which results have not been achieved prior to this invention (Compare Example 9 and Example 10 hereinbelow). In Example 10, ion concentration, temperature, time of incubation, total concentration of receptors and amount of radioligand were optimized. Furthermore, dialysis or other pre-treatment of the serum test samples is not necessary.

In order to describe more completely the present invention, there are offered below several procedures of preparing reagents, applications of the hormone-receptor binding assay and examples of clinical interest utilizing the present invention. These examples are offered by way of illustration, but not by way of limitation.

EXAMPLE 1

Purification of Human Follicle Stimulating Hormone (hFSH)

Human follicle stimulating hormone was purified from pituitary glands according to methods described by Reichert and Parlow, Endocrind. 74: 236 (1964).

Briefly, human pituitary glands were homogenized in water at pH 5.5. After 16 hours at 4° C., the preparation was centrifuged at 3000×g for 60 minutes. The supernatant was adjusted to pH 4, and combined with ammonium sulfate to a final concentration of 1.8M, stirred overnight at 4° C., and centrifuged. The supernatant which contains most of the FSH was adjusted to M ammonium sulfate, stirred overnight at 4° C. and centrifuged. The FSH was found in the pellet. The pellet was dissolved in water, dialyzed for 3 days to remove the ammonium sulfate, and lyophilized. This preparation represents "crude" FSH. Further purification can be obtained by G-200 gel filtration, DEAE ion-exchange chromatography and additional gel filtration through G-200 and G-100.

EXAMPLE 2

Purification of Other Follicle Stimulating Hormones

Follicle stimulating hormones from sheep, dolphins, pigs, cows, rats and other animals have been prepared according to methods similar to that of Example 1. Reichert, Meth. Enzymol. 37:360–380 (1975).

EXAMPLE 3

Radio-iodination of FSH

FSH was radio-iodinated according to a modification of the method of Miyachi et al. (J. Clin. Endocrinol. 34:23 (1972)). Briefly, 25 μg of FSH were dissolved in 25 μl of distilled, deionized water. To the vessel containing the hormone solution, the following was added sequentially: 25 μl of 0.5M sodium phosphate buffer (pH 7.5); 2 mCi of sodium [$^{125}$I] iodide; 0.5 IU of lactoperoxidase in 10 μl volume; 5 82 g (containing 5 ng) of hydrogen peroxide solution. Four more 5 μg aliquots of hydrogen peroxide were added at two minute intervals. After the last aliquot of hydrogen peroxide was added, the reaction mixture was incubated for another four minutes. Finally, 100 μg of transfer solution were added. The entire procedure was performed at room temperature.

If the radio-iodinated hormone was to be further processed by polyacrylamide gel electrophoresis, the transfer solution used was 16% sucrose in electrophoresis buffer. If the radio-iodinated hormone was to be further processed by G-25 gel filtration, the transfer solution used consisted of 16% sucrose, 60 mM potassium iodide and 0.01% bromophenol blue.

EXAMPLE 4

Preparation of radio-ligand reagent for radio-ligand-receptor assay (RRA) by G-25 gel chromatography Lactoperoxidase-iodinated hFSH from Example 3 was separated from free iodine by gel filtration on Sephadex G-25 columns (0.7 cm×50 cm) equilibrated with 50 mM phosphate buffer (pH 7.5), presaturated with 2 mg of bovine serum albumin (BSA). The applied sample was eluted with 50 mM phosphate buffer (pH 7.5) at 25 ml/hr. 1-ml fractions containing [$^{125}$I]-hFSH were collected for further characterization.

This is a method in the prior art for preparing radioligand reagent for RRA.

EXAMPLE 5

Preparation of Radio-Ligand Reagent for RRA by Polyacrylamide Gel Electrophoresis (PAGE)

PAGE was performed on 7.5% gels in BET buffer. 20x BET buffer was prepared by dissolving 372 g of Trizma base, 48 g of EDTA (ethylenediaminetetraacetic acid, disodium salt), 28.28 g of boric acid and 200 mg of merthiolate in 2 liters of deionized water and adjusting the pH to 8.9–10.0. 7.5% gels were prepared by combining 17.2 ml of 21% acrylamide solution (19.95 g of acrylamide and 1.05 g of BIS in BET buffer), 12.8 ml of BET buffer, 6 ml of TEMED solution (0.46 ml of stock TEMED in 100 ml of BET), and 12 ml of ammonium persulfate solution (56 mg of ammonium persulfate in 20 ml of BET). The gels, cast in 5 mm × 125 mm glass tubes, were pre-run for 45–60 minutes to remove the excess persulfate, using BET buffer in the upper chamber and 0.1% BSA in BET in the lower chamber.

The radio-iodinated hormone of Example 3 was layered onto the gels (10–12.5 μg/gel) and electrophoresed for 90 minutes (4 mamp/gel). The gels were cut into 3-mm slices and the iodinated hormone was eluted from the gel by incubation with assay buffer (10 mM HEPES (pH 7.5), 5 mM Mg $Cl_2$, 0.1M sucrose, 0.1% ovalbum) for 12 hours at 4° C. The eluted fractions were further characterized.

EXAMPLE 6

Preparation of "crude" calf testes membranes containing receptors for FSH 25 kg of frozen calf testes were decapsulated and homogenized in homogenization buffer (10 mM Tris-HCl, pH 7.5, p-hydroxymercuribenzoate, 0.15 mM 2-mercaptoethanol). 4 ml of buffer were used for each gram of tissue. The homogenate was filtered through cheese cloth and centrifuged at 7000×g for 15 minutes at 4° C. Both the supernatant and the pellet contain FSH receptors. However, the supernatant fraction contains less materials undesirable for RRA, and is preferred for use in further purification of FSH receptor.

The supernatants were filtered through cheesecloth again, pooled and concentrated by repeated passing through an Amicon H5P50-43 hollow fiber cartridge and DC-10 apparatus. Dialfiltration was continued until the volume was reduced to one liter. One liter of homogenization buffer without sucrose was added and the materials were again concentrated to one-liter volume by dialfiltration. The hollow fiber cartridge employed allows removal of materials less than 50,000 MW. Hence, membranes containing FSH receptors were retained and smaller materials, including FSH binding inhibitors, were removed.

The "crude" membranes can be stored at −80° C.

EXAMPLE 7

Preparation of "Purified" Calf Tested Membranes Containing Receptors for FSH

Part of the "crude" membranes of Example 6 was further purified by centrifugation through a 10–30% sucrose gradient in 10 mM Tris-HCl (pH 7.2), 1 mM $MgCl_2$, 1 mM $CaCl_2$, and 0.01% sodium azide. A Beckman TI-14 zonal rotor was used and the "crude" membranes (approximately 50 ml) were applied to the gradient (about 750 ml) when the rotor was spinning at 3000 rpm. The rotor speed was increased to 40,000 rpm, run for 2 hours at 4° C., and decelerated to 3000 rpm. The materials in the gradient were eluted by pumping into the rotor 40% sucrose. The material eluting between 350 and 600 ml (fractions representing approximately 21–28% sucrose) contains the greatest amount of FSH receptor activity. This material was concentrated 10-fold by dialfiltration at 4° C. using an Amicon DC-2 apparatus equipped with a H1P50 hollow fiber cartridge. Again, materials smaller than 50,000 MW were removed in the process. The concentrate was diluted with an equal volume of buffer (10 mM Tris-HCl, pH 7.2), 1 mM $MgCl_2$, 1 mM $CaCl_2$ and 0.01 % sodium azide) to reduce the sucrose concentration and reconcentrated to the previous volume.

The "purified" membranes, which contain about 773±121 fmol/mg protein, can be stored at −80° C. until further use.

EXAMPLE 8

Binding Characteristics of [$^{125}$I]-hFSH to Calf Testes FSH-Receptors

Fractions of radio-iodinated hFSH of Example 4 which were free of unincorporated sodium [$^{125}$I]-iodide were pooled. Incorporation of $^{125}$I was determined by the method of Greenwood et al. (Biochem. J. 89:114–123 (1963)). The specific activity was determined by the self-displacement method of Catt et al. (Hormone Binding and Target Cell Activation of the Testis, Dufau, M. L. and Means, A. R., eds., pp. 1–30, Plenum Press, New York (1974)). The specific activities from five preparations average 35.8±7.6 μCi/μg.

"Crude" calf testes membranes were prepared as described in Example 6. The membranes were suspended in RRA buffer (10 mM HEPES (pH 7.5), 5 mM $MgCl_2$, 0.1M sucrose), and centrifuged for 15 minutes at 30,000×g at 4° C. The membrane pellet was weighed, resuspended in RRA buffer (fortified with ovalbumin to 0.1%) at 15 mg wet weight/ml.

The RRA reaction mixtures contained membranes (200μl containing 3 mg wet weight) and varying amounts of [$^{125}$I]-hFSH in 50ml volume and 250ml of RRA buffer. Each mixture had a total volume of 0.5 ml and was incubated at 20° C. for 16 hours. After incubation each reaction mixture was centrifuged for 15 min at 28,000×g at 4° C. The bound [$^{125}$I]-hFSH was measured by counting the radioactivity of the pellets in a gamma-counter at 70% efficiency. Nonspecific binding was determined by the addition of a vast (150 to 300 fold) excess of unlabeled hFSH with all other conditions unchanged. Non-specific counts per minute bound is the radioactive hFSH bound in the presence of vast excess of unlabeled hFSH. Binding data were subjected to computer analysis by the LIGAND program of Munson and Rodbard (Anal. Biochem. 107:220–239 (1980)).

Specific binding is defined for the purpose of this application as (total counts per minute bound minus nonspecific counts per minute bound) divided by total input counts per minute under the conditions indicated in this example. Non-specific binding is defined for the purpose of this application as non-specific counts per minute bound divided by total input counts per minute under the conditions indicated in this example. The results were:

(d) Computer Scatchard plot analysis (Scatchard, G., Ann. N.Y. Acad. Sci. 51:660–672 (1949)) of specific binding (total binding minus non-specific binding) data indicates that [$^{125}$I]-FSH binds to a single high affinity receptor ($K_d = 2.2 \times 10^{-10} M^{-1}$) on the calf testes membrane under the assay conditions. See FIGS. 1A and 1B.

Figure 2A:
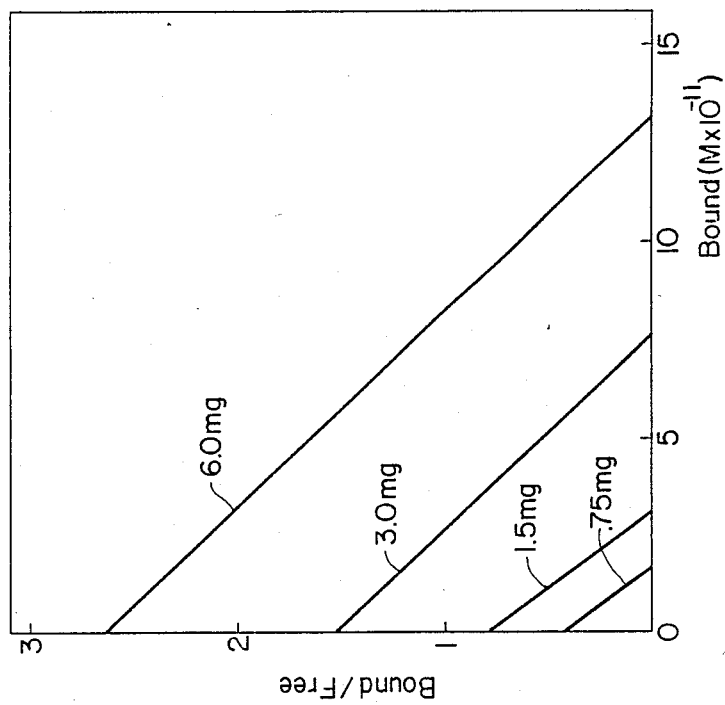
FIG. 2A shows Scatchard Plot analyses of [$^{125}$I]-hFSH binding isotherms. Each isotherm represents a different amount of FSH receptors provided.

(e) The number of high affinity receptors/mg of calf testes membranes, 11.1 fmol/mg, was independent of membrane concentrations between 1.5 and 12 mg/ml. See FIGS. 2A and 2B.

EXAMPLE 9

RRA on "Hypox" Serum (a) G-25 gel chromatographed radio-ligand of Example 4 and rat membranes were used as reagents in a RRA reaction. Rat testes tissue was homogenized in 10mM phosphate pH 7.5 containing 5mM $MgCl_2$, 0.1M sucrose, 0.1% egg albumin. The homogenate was filtered through cheese cloth and centrifuged at $1500 \times g$ for 10 minutes. The pellet was resuspended in the same buffer, filtered through cheese cloth again and aliquoted for RRA. The test sample was a serum sample from a "hypox" patient, i.e., a sample free of hFSH. Varying amounts of the test sample were added to compete for receptor sites.

Figure 3:
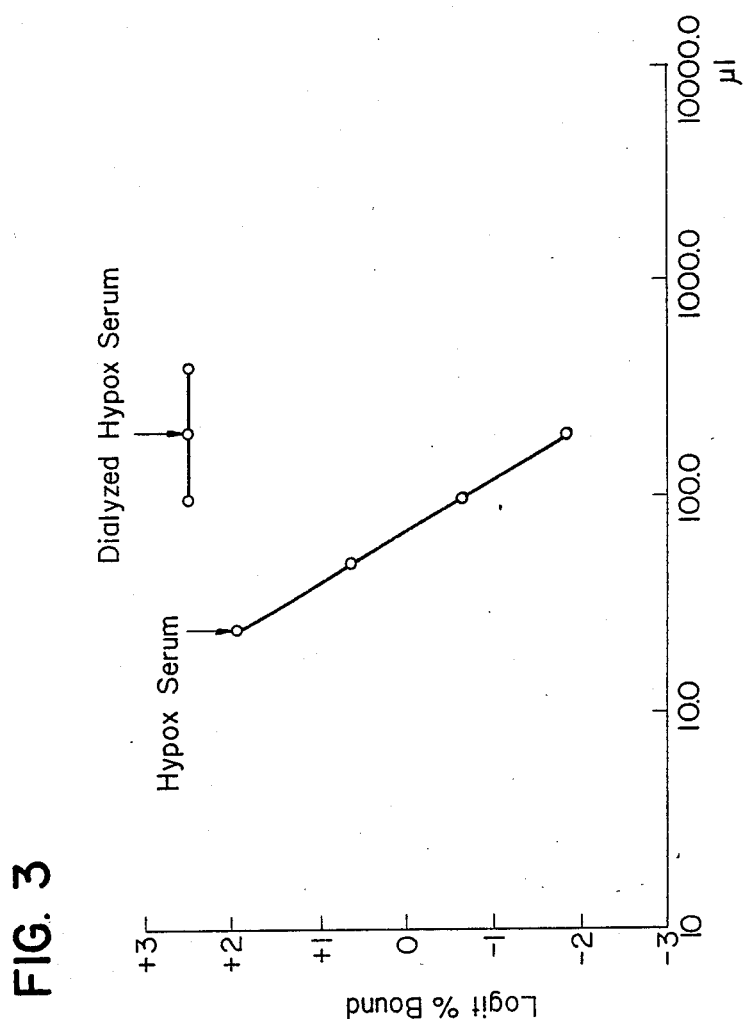

(b) The same as in (a) except that the "hypox" serum was dialyzed prior to the RRA reaction.
The results are shown in FIG. 3. A comparison of the results from (a) and (b) (FIG. 3) indicates the nonspecific interference effects of serum samples when reagents of the prior art were used.

EXAMPLE 10

Improved RRA On FSH-Free Serum

In this example, the reaction buffer was 50 mM HEPES(pH 7.5), 10 mM $CaCl_2$, 5 mM $MgCl_2$, 2mM EDTA, 0.1% merthiolate, sucrose and 0.1% ovalbumin. The total reaction volume was 0.4 ml. The incubation was 20° C. for 20–24 hours. After incubation, 0.5 ml of 50 mM sodium phosphate buffer (pH 7.5) and 0.9 ml of polyethyleneglycol was added. The mixture was then centrifuged for 40 minutes at $2000 \times g$ and the supernatant decanted. The radioactivity in the pellet was then counted in an automatic gamma counter.

(a) PAGE purified radio-ligand of Example 5 (2–2.5 ng or 150–200 kcpm) and "purified" membranes of Example 7 were used as reagents in a RRA reaction. The test sample was a serum sample free from FSH as in Example 9.

(b) The same as in (a) except that 0.5 to 50 ng of highly purified unlabeled hFSH was added to the FSH-free serum sample.

Figure 4:
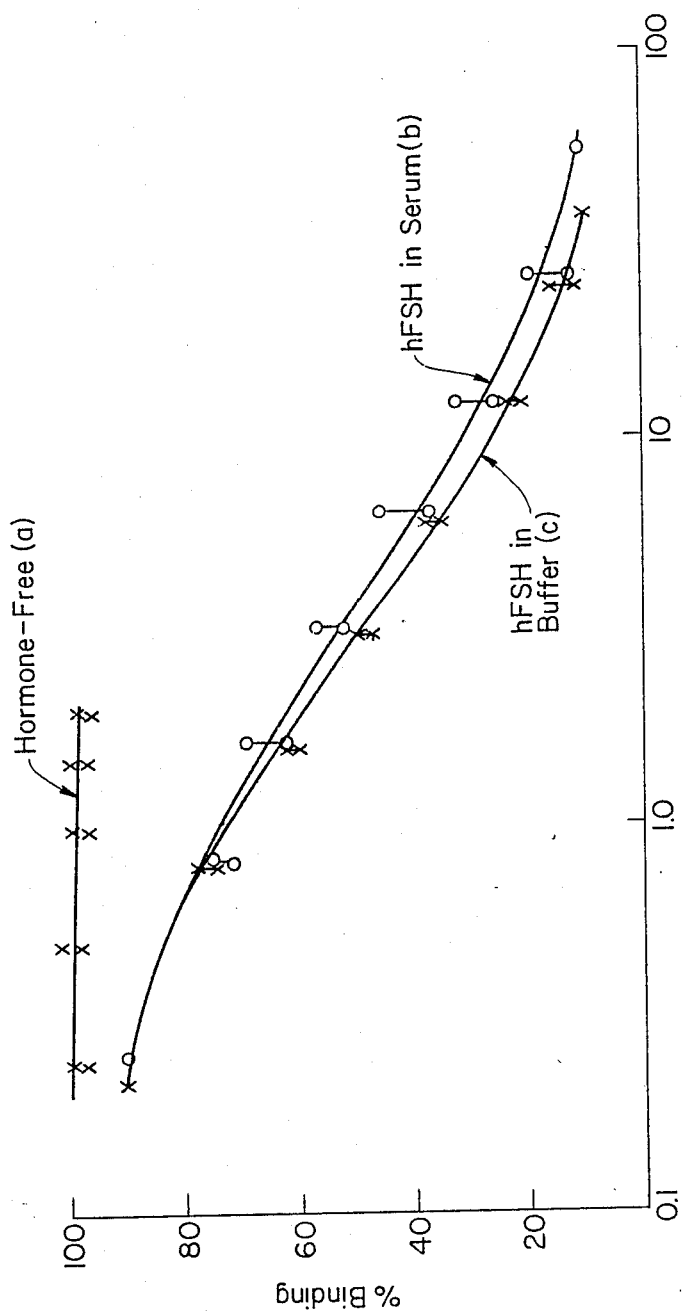
FIG. 4 illustrates the absence of non-specific interfering effects of serum without dialysis or other pretreatment when improved reagents of this invention are used.

(c) The same as in (b) except that reaction buffer was substituted for FSH-free serum. A comparison of the results from (a), (b) and (c) (FIG. 4) indicates that the interference effects of serum were absent when reagents provided by the present invention were used.

EXAMPLE 11

Determination of hFSH in a Serum Sample from an Infertile Patient Suffering from Premature Ovarian Failure (POF)

RRA reactions were performed as in Example 10 with or without dialysis of the POF serum sample to remove materials of less than 25,000 daltons. Radioimmunoassay (RIA) reactions were performed on parallel samples for comparison. The results are indicated in Table 1 below.

TABLE 1

|  | RRA | RIA |
| --- | --- | --- |
| Undialyzed sample | 430 mIU/ml | 96 mIU/ml |
| Dialyzed sample | 101 mIU/ml | 92 mIU/ml |
| Passed through material | 104 mIU/ml | 1 mIU/ml |

These results indicate that the POF serum contains a FSH-like factor which is dialyzable and which is not present in normal sera. This conclusion can be reached because in accordance with the invention, normal sera do not give FSH-like interfering effects. (See Example 10 above.)

EXAMPLE 12

Determination of FSH in a Serum Sample from POF Patients in Spontaneous Remission The same reactions as in Example 11 were performed on serum samples from two patients whose POF was in spontaneous remission. Patient B became pregnant subsequent to sampling. The results are indicated in Table 2 below.

TABLE 2

|  | RRA | RIA |
| --- | --- | --- |
| Patient A |  |  |
| Undialyzed sample | FSH undetectable** | FSH undetectable** |
| Dialyzed sample | FSH undetectable** | FSH undetectable** |
| Patient B |  |  |
| Undialysed sample | 5.6 mIU/ml | 4.3 mIU/ml |

**5.6 mIU/ml which is the lower limit of detection

Having described the invention with particular reference to certain embodiments, it will be obvious to those skilled in the art to which the invention pertains after understanding the invention, that various changes and modifications may be made without departing from the spirit and scope of the invention as defined by the appended claims.

What is claimed is:

1. In a method for the determination of follicle stimulating hormone in a sample, comprising the steps of:
   (a) contacting said sample with a purified follicle stimulating hormone receptor preparation capable of selectively binding said hormone;
   (b) providing a signalling entity for signalling whether said binding has taken place; and
   (c) observing said signalling entity to determine the presence of said hormone in said sample, the improvement comprising said signalling entity being a substantially pure follicle stimulating hormone labeled with a detectable label, in which labeled hormone the ratio of specific binding to non-specific binding is at least about 5 when measured using a partially purified calf testes plasma membrane preparation containing from about 5 to about 25 fmol of receptors per milligram of membrane wet weight, and said purified follicle stimulating hormone receptor preparation having at least about 600 fmol/mg protein of high affinity receptors for follicle stimulating hormone.

2. In a method for the determination of follicle stimulating hormone in a sample, comprising the steps of:
   (a) contacting said sample with a purified follicle stimulating hormone receptor preparation capable of selectively binding said hormone;

(b) providing a signalling entity for signalling whether said binding has taken place; and (c) observing said signalling entity to determine the presence of said hormone in said sample, the improvement comprising said signalling entity being a substantially pure follicle stimulating hormone labeled with a detectable label, prepared from an unpurified labeled follicle stimulating hormone and characterized as follows:

(i) the substantially pure labeled follicle stimulating hormone co-migrates as a single band with unlabeled follicle stimulating hormone when electrophoresed on 7.5% polyacrylamide gel with an acrylamide to BIS ratio of about 19:1 in an electrophoresis buffer containing 9.3 g of tris(hydroxymethyl)tetraacetic acid (disodium salt), 0.7 g of boric acid and 5 mg of merthiolate per liter of water at a pH of from 8.9 to 10; and (ii) when the unpurified, labeled follicle stimulating hormone is chromatographed on a G-25 column and a portion of the labeled follicle stimulating hormone of any fraction from the column having the same amount of detectable label as used in part (i) is electrophoresed as described in part (i), the amount of detectable label found in the single band of part (i) is at least about three times the amount of detectable label in the co-migrating band of material from the fraction of the column;

and said purified follicle stimulating hormone receptor preparation having at least about 600 fmol!/mg protein of high affinity receptors for follicle stimulating hormone.

3. The method of claim 1 or 2, wherein said contact between said sample and said purified follicle stimulating hormone receptor preparation recited in step (a) comprises an incubation in a buffer comprising about 10 nM $CaCl_2$, about 5 mM $MgCl_2$, about 2 mM ethylendediamine-tetraacetic acid, about 0.1merthiolate, and about 0.15M sucrose for about 20–24 hours at about 20° C.

4. The method of claim 1 or 2, wherein said labeled follicle stimulating hormone is labeled with a radioactive label.

5. The method of claim wherein said radioactive label is $^{125}I$ or $^{131}I$.

6. The method of claim 5, wherein said sample is an aqueous sample.

7. The method of claim 6, wherein said aqueous sample is a biological fluid.

8. The method of claim 7, wherein the biological fluid is from a human, sheep, rat, pig, cow, dolphin or porpoise.

9. The method of claim 8, wherein said biological fluid is serum or plasma.

* * * * *